(12) United States Patent
Yang et al.

(10) Patent No.: US 11,486,810 B2
(45) Date of Patent: Nov. 1, 2022

(54) FLUORESCENCE SENSOR FOR MEASURING MICROALGAE AND METHOD OF OPERATING THE SAME

(71) Applicant: ELECTRONICS AND TELECOMMUNICATIONS RESEARCH INSTITUTE, Daejeon (KR)

(72) Inventors: Woo Seok Yang, Daejeon (KR); Sung Q Lee, Daejeon (KR); Chang Han Je, Daejeon (KR); Gunn Hwang, Seoul (KR); Hyung Kun Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 484 days.

(21) Appl. No.: 16/709,986

(22) Filed: Dec. 11, 2019

(65) Prior Publication Data

US 2020/0191695 A1 Jun. 18, 2020

(30) Foreign Application Priority Data

Dec. 13, 2018 (KR) .......................... 10-2018-0161116

(51) Int. Cl.
  *G01N 15/06* (2006.01)
  *G01N 21/64* (2006.01)
  *C12Q 1/02* (2006.01)
(52) U.S. Cl.
  CPC ............... *G01N 15/06* (2013.01); *C12Q 1/02* (2013.01); *G01N 21/6486* (2013.01); *G01N 2015/0693* (2013.01)
(58) Field of Classification Search
  CPC ............... G01N 15/06; G01N 21/6486; G01N 2015/0693; C12Q 1/02
  See application file for complete search history.

(56) References Cited

U.S. PATENT DOCUMENTS 5,225,089 A * 7/1993 Benes .................. B01D 21/283
                                            366/127
5,626,767 A * 5/1997 Trampler ............... G10K 11/04
                                            435/261

(Continued)

FOREIGN PATENT DOCUMENTS

JP         06241977 A  *  9/1994
JP        H06241977 A     9/1994
JP         06241977 A  *  4/1999

OTHER PUBLICATIONS

Seung Hyun Cho et al., "Finite Element Analysis of a Particle Manipulation System Using Ultrasonic Standing Wave", DOI : 10.5050/KSNVE.2010.20.1.003, pp. 39.

(Continued)

*Primary Examiner* — Dominic J Bologna
*Assistant Examiner* — Jarreas C Underwood
(74) *Attorney, Agent, or Firm* — Rabin & Berdo, P.C.

(57) ABSTRACT

The present invention relates to a fluorescence sensor for measuring microalgae and a method of operating the same. The fluorescence sensor for measuring the microalgae includes a fluorescence measurement unit including a light emitter configured to irradiate excitation light onto a measurement region and a detector configured to measure fluorescence emitted from the measurement region, an algae control unit configured to form a node and an antinode of an ultrasonic standing wave in the measurement region to control an algal density, and a signal processing unit configured to calculate the algal density using fluorescence intensity signals according to an operation mode of the algae control unit.

14 Claims, 10 Drawing Sheets

(56) References Cited

U.S. PATENT DOCUMENTS

| | | | |
|---|---|---|---|
| 7,340,957 B2* | 3/2008 | Kaduchak | B01D 21/28 73/570.5 |
| 8,263,407 B2* | 9/2012 | Goddard | G01N 15/1484 436/63 |
| 8,425,749 B1* | 4/2013 | Ravula | B03C 5/026 181/141 |
| 9,733,171 B2 | 8/2017 | Ward et al. | |
| 10,113,949 B2 | 10/2018 | Bierganns et al. | |
| 2003/0048445 A1* | 3/2003 | Tokhtuev | G01N 33/1886 356/411 |
| 2004/0005582 A1* | 1/2004 | Shipwash | G01N 33/54366 435/7.1 |
| 2007/0119239 A1* | 5/2007 | Priev | G01N 15/06 73/662 |
| 2008/0245745 A1* | 10/2008 | Ward | G01N 1/4077 210/94 |
| 2009/0029870 A1* | 1/2009 | Ward | G01N 27/447 210/695 |
| 2009/0107241 A1* | 4/2009 | Goddard | G01N 15/1404 73/570.5 |
| 2009/0260767 A1* | 10/2009 | Gerli | G01N 33/343 162/49 |
| 2010/0167276 A1* | 7/2010 | Rohwer | G01N 33/56911 435/6.12 |
| 2012/0086938 A1* | 4/2012 | Folkenberg | G01N 1/4077 356/246 |
| 2016/0341724 A1 | 11/2016 | Kim et al. | |
| 2017/0248513 A1* | 8/2017 | Liu | G01N 29/022 |
| 2017/0348735 A1* | 12/2017 | Sinha | G01N 15/1404 |
| 2017/0350824 A1* | 12/2017 | Olsen | G01N 21/85 |
| 2018/0156755 A1 | 6/2018 | Jeong et al. | |
| 2019/0368999 A1* | 12/2019 | Kambayashi | G01N 21/15 |

OTHER PUBLICATIONS

Cosima Koch et al., "Ultrasound-Enhanced Attenuated Total Reflection Mid-infrared Spectroscopy In-Line Probe: Acquisition of Cell Spectra in a Bioreactor", Analytical Chemistry, pp. 2314-2320, Jan. 12, 2015.

* cited by examiner

FLUORESCENCE SENSOR FOR MEASURING MICROALGAE AND METHOD OF OPERATING THE SAME

CROSS-REFERENCE TO RELATED APPLICATION

This application claims priority to and the benefit of Korean Patent Application No. 10-2018-0161116, filed on Dec. 13, 2018, the disclosure of which is incorporated herein by reference in its entirety.

BACKGROUND

1. Field of the Invention

The present invention relates to a fluorescence sensor for measuring microalgae and a method of operating the same.

2. Discussion of Related Art

Methods using the fluorescence sensor for measuring algae according to the related art have problems in that measurement accuracy is low and a measurement lower limit is high.

Since detected fluorescence intensity is caused not only by a pigment contained in algae to be measured but also by a pigment dissolved in water that is excluded from measurement, there is a problem in that measurement accuracy is low.

In addition, when an algal density in a measurement region is low, there is a problem in that measurement noise caused by a pigment dissolved in water is greater than a measurement signal caused by a pigment contained in the algae so that a measurement lower limit becomes higher.

SUMMARY OF THE INVENTION

The present invention is directed to providing a fluorescence sensor for measuring microalgae which has high measurement accuracy and a low measurement lower limit, and a method of operating the same.

According to an aspect of the present invention, there is provided a fluorescence sensor for measuring microalgae that includes a fluorescence measurement unit including a light emitter configured to irradiate excitation light onto a measurement region and a detector configured to measure fluorescence emitted from the measurement region, an algae control unit configured to form a node and an antinode of an ultrasonic standing wave in the measurement region to control an algal density, and a signal processing unit configured to calculate the algal density using fluorescence intensity signals according to an operation mode of the algae control unit.

According to an aspect of the present invention, there is provided a fluorescence sensor for measuring microalgae that includes an optical measurement unit including a fluorescence measurement unit configured to measure fluorescence emitted from a measurement region when excitation light is irradiated onto the measurement region and a turbidity measurement unit configured to measure scattered light emitted from the measurement region when incident light is irradiated onto the measurement region, an algae control unit configured to form a node and an antinode of an ultrasonic standing wave in the measurement region to control an algal density, and a signal processing unit configured to calculate the algal density using a fluorescence intensity signal and a scattered light intensity signal according to an operation mode of the algae control unit.

According to an aspect of the present invention, there is provided a method of operating a fluorescence sensor for measuring microalgae that includes measuring total fluorescence intensity emitted by irradiating excitation light in a state in which there is no ultrasonic wave in a measurement region, measuring noise fluorescence intensity by forming a node of an ultrasonic standing wave in the measurement region, and calculating an algal density using signal fluorescence intensity which is a result of subtracting the noise fluorescence intensity from the total fluorescence intensity.

DETAILED DESCRIPTION OF EXEMPLARY EMBODIMENTS

These and other objects, advantages, and features of the present invention and methods for accomplishing the same will be more clearly understood from embodiments described below with reference to the accompanying drawings.

However, the present invention is not limited to the following embodiments but may be implemented in various different forms. Rather, these embodiments are provided so that this disclosure will fully convey the objects, configurations, and effects of the present invention to those skilled in the art. The scope of the present invention is defined solely by the appended claims.

Terms used in this specification are to describe the embodiments and are not intended to limit the present invention. As used herein, singular expressions, unless defined otherwise in contexts, include plural expressions. It will be further understood that the terms "comprises," "comprising," "includes," and/or "including," when used herein, specify the presence of stated components, steps, operations, and/or elements, but do not preclude the presence or addition of one or more other components, steps, operations, and/or elements.

Hereinafter, the background of the present invention will be described to facilitate the understanding of those skilled in the art, and then, embodiments of the present invention will be described.

Microalgae known as phytoplankton are microscopic aquatic plants that grow in water and live autotrophically through photosynthesis play an important role as primary producers of an aquatic ecosystem. However, when the microalgae proliferate excessively, the microalgae cause green algae, red algae, and the like to contaminate water.

All algae, including dinoflagellates that cause a red tide, contain a chlorophyll pigment necessary for photosynthesis and contain other pigments other than chlorophyll according to types of the algae. Blue-green algae that cause an algal bloom contain phycocyanin and phycoerythrin.

In order for water quality management to be executed, a fluorescence sensor is usually used to measure a biovolume (volume of algae contained in 1 L of water in a measurement region) or a cell density (cell number of algae contained in 1 mL of water in a measurement region) of algae in water.

When excitation light is irradiated onto a measurement region, algae absorb light energy through a pigment and use a portion of the absorbed light for metabolic activity through photosynthesis and emit the rest of the absorbed light as fluorescence and heat. In this case, fluorescence intensity is detected to calculate a pigment concentration of algae and a biovolume and cell density (hereinafter, collectively referred to as "density") corresponding to the pigment concentration.

A method using a fluorescence sensor for measuring algae according to the related art has an advantage in that an algal density is measurable in real time in the field but also has disadvantages in that measurement accuracy is low and a measurement lower limit is high.

One of major causes of the low measurement accuracy is that the detected fluorescence intensity is caused not only by a pigment contained in algae to be measured but also by a pigment dissolved in water that is excluded from measurement.

In particular, when an algal density in a measurement region is low, measurement noise caused by a pigment dissolved in water is greater than a measurement signal caused by a pigment contained in the algae and thus a measurement lower limit becomes higher.

The present invention has been proposed to solve the above-described problems and provides a fluorescence sensor for measuring microalgae, which has high accuracy due to adjusting a density of microalgae of a measurement region using an ultrasonic control module, and a method of operating the same.

The present invention is derived from a task performed as a part of the information, communication and broadcasting research and development project of Korea Ministry of Science and ICT (Project Number: 1711070420 and Project Name: Space-time complex artificial intelligence blue-green algae prediction technology based on direct-readable water quality complex sensor and hyperspectral image).

Figure 1:
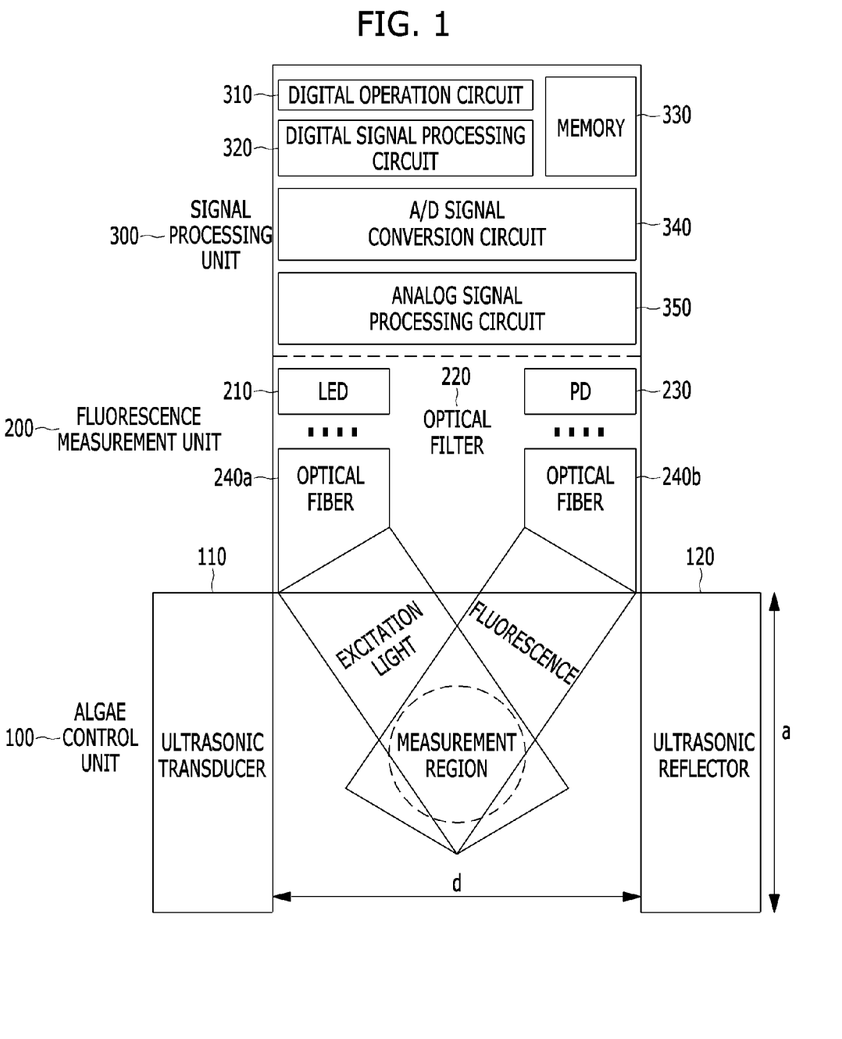
FIG. 1 is a vertical cross-sectional view illustrating a fluorescence sensor for measuring microalgae according to an embodiment of the present invention.
Figure 2:
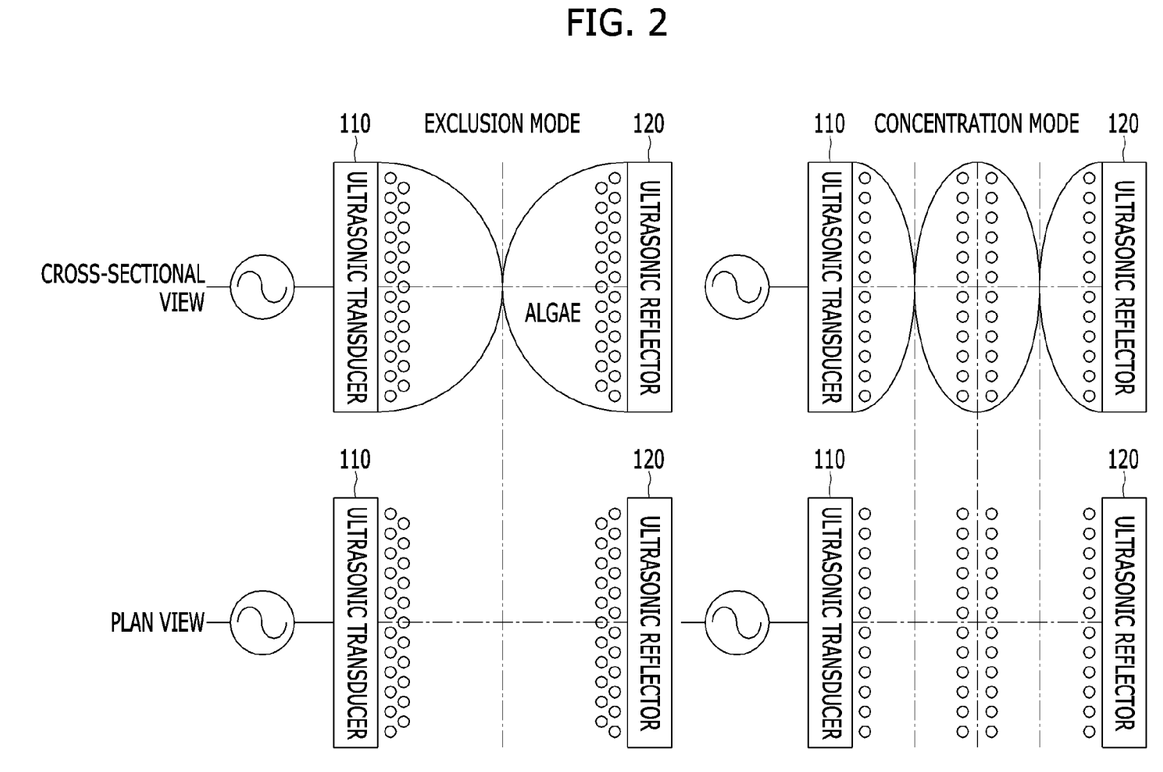
FIG. 2 shows vertical and horizontal cross-sectional schematic views illustrating an operation principle of an algae control unit included in the fluorescence sensor for measuring the microalgae according to the embodiment of the present invention.

FIG. 1 is a vertical cross-sectional schematic view illustrating a fluorescence sensor for measuring microalgae according to an embodiment of the present invention, FIG. 2 shows vertical and horizontal cross-sectional schematic views illustrating an operation principle of an algae control unit included in the fluorescence sensor.

Referring to FIGS. 1 and 2, the fluorescence sensor for measuring the microalgae according to the embodiment of the present invention includes a fluorescence measurement unit 200 including a light emitter configured to irradiate excitation light onto a measurement region and a detector configured to measure fluorescence emitted from the measurement region, an algae control unit 100 configured to adjust an algal density by forming a node and an antinode of an ultrasonic standing wave in the measurement region, and a signal processing unit 300 configured to calculate the algal density using fluorescence intensity signals according to an operation mode of the algae control unit 100.

The algae control unit 100 includes an ultrasonic pair of an ultrasonic transducer 110 and an ultrasonic reflector 120 disposed opposite to the ultrasonic transducer 110 and adjusts an algal density by forming a node and an antinode of an ultrasonic standing wave in a measurement region positioned at a center between the ultrasonic transducer 110 and the ultrasonic reflector 120.

The signal processing unit 300 outputs fluorescence intensity signals according to an operation state of the algae control unit 100 and calculates a corrected algal density by comparing and calculating the fluorescence intensity signals.

As shown in FIG. 1, with respect to the fluorescence measurement unit 200, the algae control unit 100 is disposed at a lower side close to the measurement region, and the signal processing unit 300 is disposed at an upper side far away from the measurement region.

In the fluorescence measurement unit 200, the light emitter includes a light source such as a light-emitting diode (LED) or laser diode (LD), an optical filter 220 disposed on a light-emitting surface of the LED to transmit excitation light having a specific wavelength band, and an optical fiber 240a configured to transfer the excitation light so as to be irradiated at an angle ranging from 25° to 45° with respect to a direction perpendicular to the light-emitting surface at a certain distance from the measurement region.

The detector includes an element such as a photodiode (PD) 230 or a photomultiplier tube (PMT), the optical filter 220 disposed on a light-receiving surface of the PD 230 to transmit fluorescence having a specific wavelength band, and an optical fiber 240b configured to receive fluorescence emitted from the measurement region at a certain distance and transfer the fluorescence so as to be incident at an angle ranging from 25° to 45° with respect to a direction perpendicular to the PD 230.

In the fluorescence measurement unit 200, the excitation light includes at least one of light beams having center wavelengths ranging from 460 nm to 470 nm, 590 nm to 600 nm, and 520 nm to 530 nm, which are respectively absorbed by chlorophyll a, phycocyanin, and phycoerythrin pigments contained in algae. The fluorescence includes at least one of light beams having central wavelengths of 685 nm, 650 nm, and 570 nm, which are respectively emitted by the chlorophyll a, phycocyanin, and phycoerythrin pigments contained in the algae.

In an example of constituting the fluorescence measurement unit 200, in the case of a fluorescence sensor for measuring microalgae, which is for monitoring an algal bloom and a red tide in fresh water, the fluorescence measurement unit 200 includes two light emitters configured to emit first excitation light and second excitation light having wavelength bands of 470±15 nm and 590±15 nm, which are respectively absorbed by chlorophyll a and phycocyanin pigments, and two detectors configured to measure first fluorescence and second fluorescence having center wavelengths of 685±20 nm and 650±10 nm which are respectively emitted by the chlorophyll a and phycocyanin pigments.

In another example of constituting the fluorescence measurement unit 200, in the case of a fluorescence sensor for measuring microalgae which monitors an algal bloom and a red tide in seawater, the fluorescence measurement unit 200 includes two light emitters configured to emit first excitation light and second excitation light having wavelength bands of 470±15 nm and 525±15 nm, which are respectively absorbed by chlorophyll a and phycoerythrin pigments, and two detectors configured to measure first fluorescence and second fluorescence having center wavelengths of 685±20 nm and 570±20 nm which are respectively emitted by the chlorophyll a and phycoerythrin pigments.

In the algae control unit 100, an ultrasonic wave has a frequency range including a preset range (for example, 37.5 kHz to 200 kHz) and is a longitudinal wave in which algae are moved in the same direction as a traveling direction of the ultrasonic wave.

A pair of the ultrasonic transducer 110 and the ultrasonic reflector 120 are provided, and a range of a length (that is, a distance d between the ultrasonic transducer and the ultrasonic reflector) includes a preset range (for example, 7.5 mm to 20 mm).

The algae control unit 100 is operated in an exclusion mode of excluding algae having a negative acoustic contrast factor by applying an alternating current, which has a frequency corresponding to a wavelength ($\lambda=2d$) that is twice the distance d, to the ultrasonic transducer 110 and forming a node of an ultrasonic standing wave in the measurement region positioned at the center of the ultrasonic pair.

In addition, the algae control unit 100 is operated in a concentration mode of concentrating algae by applying an alternating current, which has a frequency corresponding to a wavelength ($\lambda=d$) that is equal to the distance d, to the ultrasonic transducer 110, and forming an antinode of an ultrasonic standing wave in the measurement region.

In this case, unlike the algae, other particles having a positive acoustic contrast factor are concentrated in a region in which the node of the ultrasonic standing wave is formed and are excluded from a region in which the antinode is formed unlike the algae.

An ultrasonic near field length is a value obtained by dividing the square ($a^2/\pi$ for a quadrangle) of a diameter of the ultrasonic transducer by four times a wavelength ($4\lambda$). When the ultrasonic near field length is exceeded, intensity of an ultrasonic wave is rapidly decreased as a traveling distance of the ultrasonic wave is increased.

Accordingly, an area of the ultrasonic transducer 110 and the ultrasonic reflector 120 corresponding thereto may be greater than or equal to a constant value ($4\pi\lambda d$) such that the length (distance d) of the ultrasonic pair is less than or equal to the near field length ($a^2/4\pi\lambda$ for a quadrangle).

That is, as described above, in the exclusion mode in which $\lambda=2d$, the area of the ultrasonic transducer 110 may be greater than or equal to $8\pi d^2$ (about $25d^2$), and in the case of the concentration mode in which $\lambda=d$, the area of the ultrasonic transducer 110 may be greater than or equal to 4 $\pi d^2$ (about $13d^2$).

In the algae control unit 100, the ultrasonic transducer 110 includes a lead zirconate titanate (PZT) ceramic or lead magnesium niobate-lead titanate (PMN-PT) single crystal element, and the ultrasonic reflector 120 includes a titanium metal or copper-titanium alloy plate.

The signal processing unit 300 includes an analog signal processing circuit 350, an analog/digital (A/D) signal conversion circuit 340, a digital signal processing circuit 320, a digital operation circuit 310, and a memory 330.

The signal processing unit 300 outputs total fluorescence intensity ($I_T$) in a state in which there is no ultrasonic wave in the measurement region, noise fluorescence intensity ($I_N$) in a state in which a node of an ultrasonic wave is formed in the measurement region and thus algae are excluded, and concentrated total fluorescence intensity ($I_{TF}$) in a state in which an antinode of an ultrasonic wave is formed in the measurement region and thus algae are concentrated. Then, by comparing signal fluorescence intensity ($I_S$) obtained by subtracting the noise fluorescence intensity ($I_N$) from the total fluorescence intensity ($I_T$) with the noise fluorescence intensity ($I_N$), when the signal fluorescence intensity ($I_S$) is greater than or equal to the noise fluorescence intensity ($I_N$), the signal processing unit 300 calculates a corrected algal density from the signal fluorescence intensity ($I_S$), and when the signal fluorescence intensity ($I_S$) is less than the noise fluorescence intensity ($I_N$), the signal processing unit 300 calculates a corrected algal density from concentrated signal fluorescence intensity ($I_{SF}$) obtained by subtracting the noise fluorescence intensity ($I_N$) from the concentrated total fluorescence intensity ($I_{TF}$).

Figure 3:
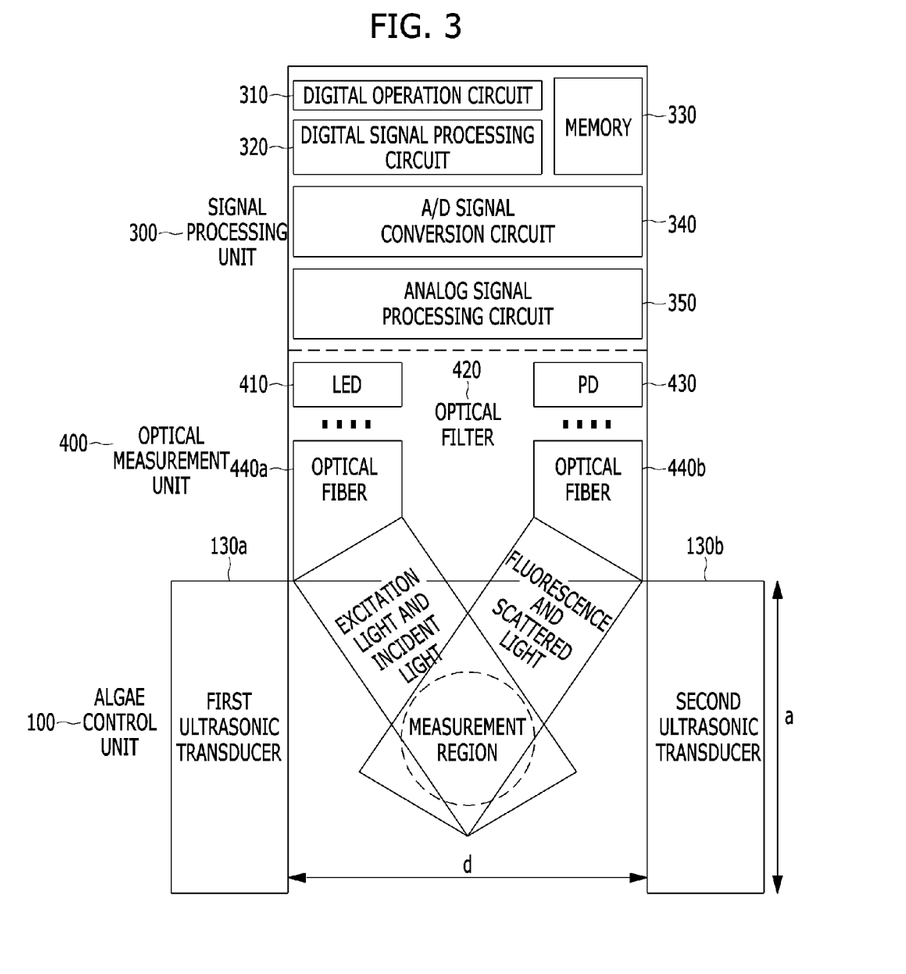
FIG. 3 is a vertical cross-sectional view illustrating a fluorescence sensor for measuring microalgae according to another embodiment of the present invention.
Figure 4A:
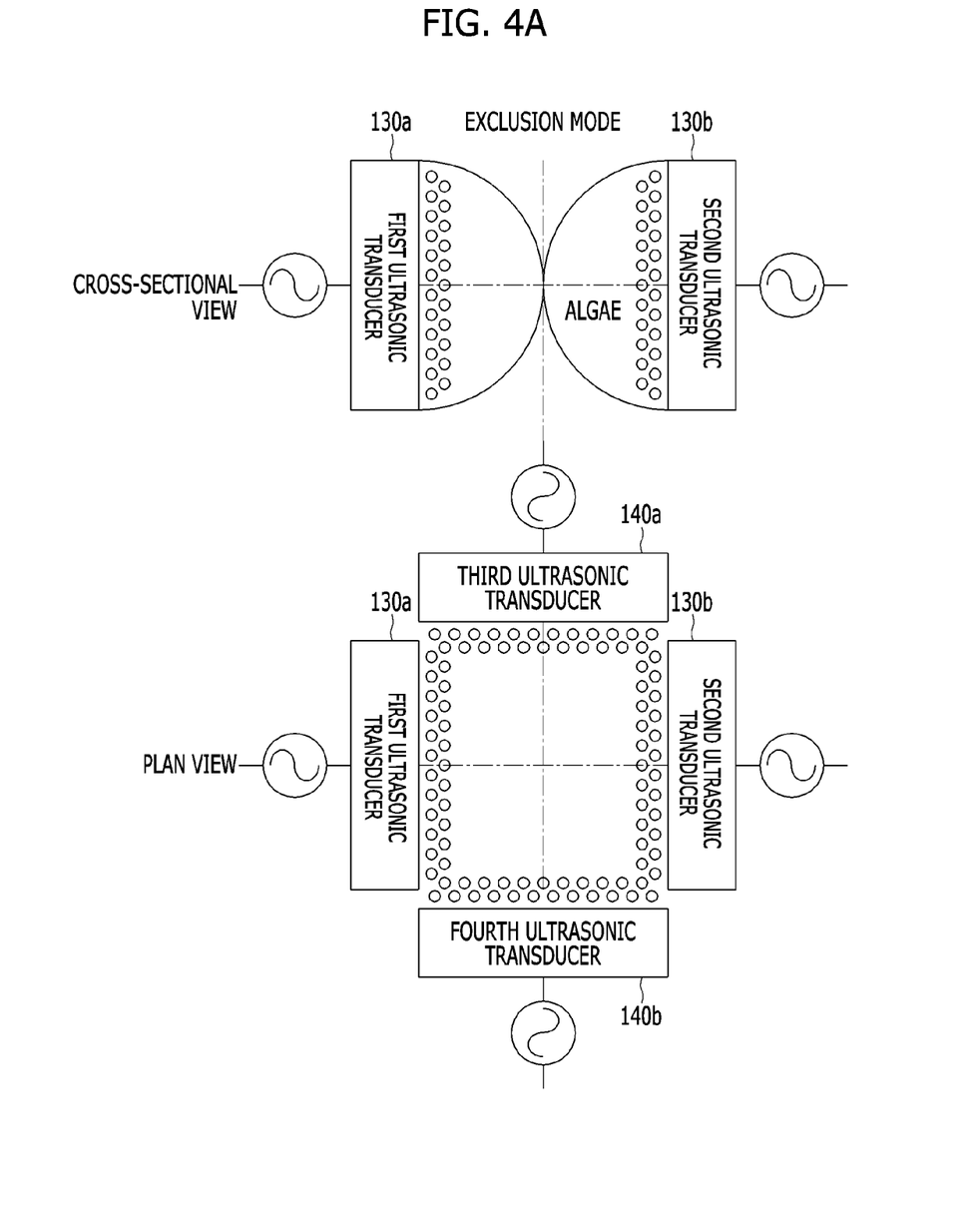
FIG. 4A and FIG. 4B show vertical and horizontal cross-sectional schematic views illustrating an operation principle of an algae control unit included in the fluorescence sensor for measuring the microalgae according to another embodiment of the present invention.
Figure 4B:
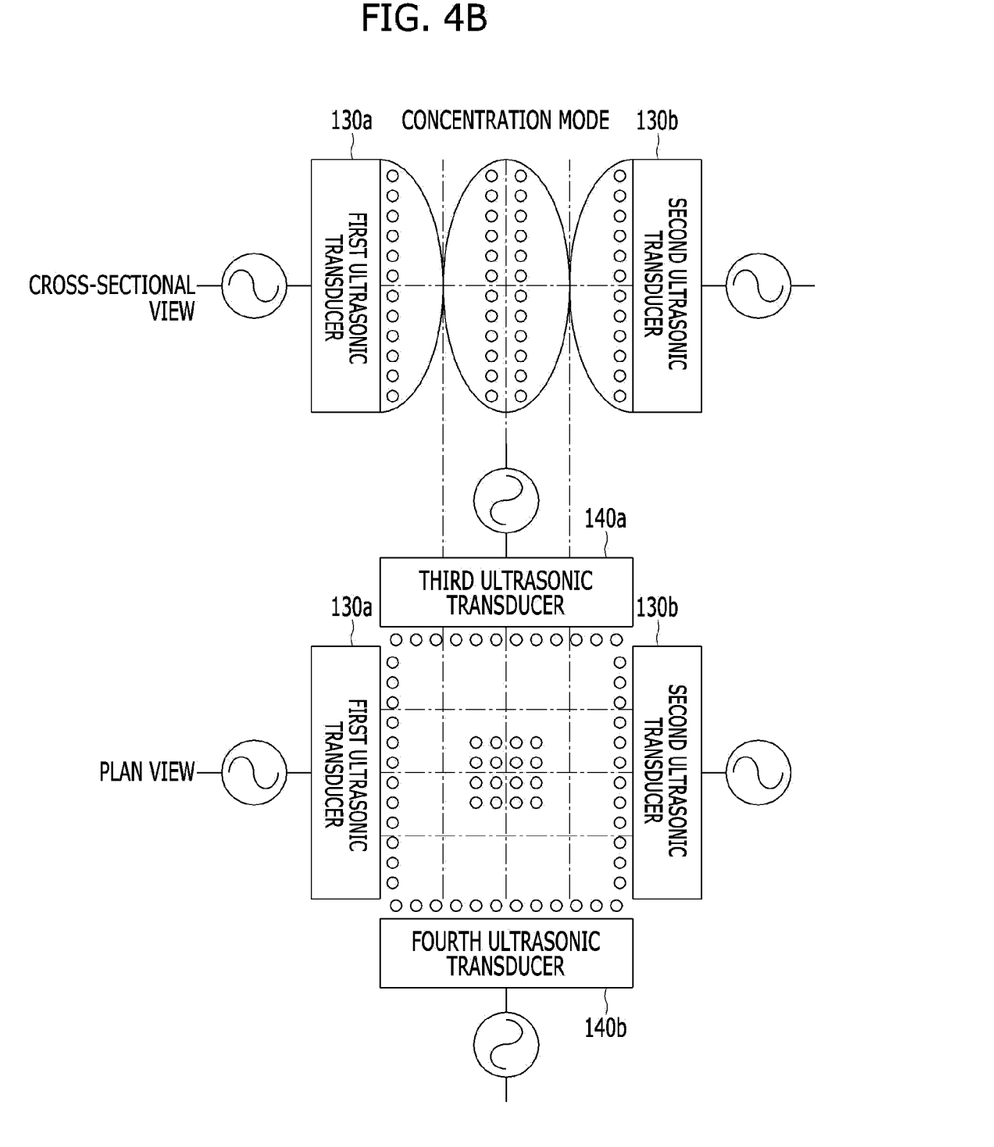

FIG. 3 is a vertical cross-sectional schematic view illustrating a fluorescence sensor for measuring microalgae according to another embodiment of the present invention, and FIG. 4A and FIG. 4B show vertical and horizontal cross-sectional schematic views illustrating an operation principle of an algae control unit included in the fluorescence sensor.

Referring to FIGS. 3 and 4, the fluorescence sensor for measuring the microalgae according to another embodiment of the present invention includes an optical measurement unit 400 including a fluorescence measurement unit configured to measure fluorescence emitted from a measurement region when excitation light is irradiated onto the measurement region and a turbidity measurement unit configured to measure scattered light emitted from the measurement region when incident light is irradiated onto the measurement region, an algae control unit 100 configured to adjust an algal density by forming a node and an antinode of an ultrasonic standing wave in the measurement region, and a signal processing unit 300 configured to calculate the algal density using a fluorescence intensity signal and a scattered light intensity signal according to an operation mode of the algae control unit 100.

The fluorescence measurement unit includes a light emitter configured to irradiate excitation light onto the measurement region including algae and a detector configured to measure fluorescence emitted from the measurement region.

The turbidity measurement unit includes a light emitter configured to irradiate incident light onto the measurement region and a detector configured to measure scattered light emitted from the measurement region.

The algae control unit 100 includes an ultrasonic pair of a first ultrasonic transducer 130a and a second ultrasonic transducer 130b disposed opposite to the first ultrasonic transducer 130a and adjusts an algal density by forming a node and an antinode of an ultrasonic standing wave in a measurement region positioned at a center between the first ultrasonic transducer 130a and the second ultrasonic transducer 130b.

The signal processing unit 300 outputs fluorescence intensity signals according to an operation state of the algae control unit 100 and calculates a corrected algal density by comparing and calculating the fluorescence intensity signals.

As shown in FIG. 3, with respect to the optical measurement unit 400, the algae control unit 100 is disposed at a lower side, and the signal processing unit 300 is disposed at an upper side far away from the measurement region.

The configuration of the fluorescence measurement unit of the optical measurement unit 400 is the same as the configuration of the fluorescence measurement unit according to the embodiment of the present invention described with reference to FIG. 1.

In the turbidity measurement unit, the light emitter and the detector include an LED 410, a light-receiving element such as a PD 430, a filter 420, and an optical fiber 440b, similar to the fluorescence measurement unit, and a central wavelength range of the incident light and the scattered light includes a preset length (for example, 860 nm).

As shown in FIG. 4A and FIG. 4B, in the algae control unit 100, two ultrasonic pairs of the ultrasonic transducers 130a and 130b and ultrasonic transducers 140a and 140b, which are opposite to each other, are orthogonally arranged with each other. A length d of the ultrasonic pairs is in a preset range (for example, 10 mm to 20 mm), and alternating currents applied to the ultrasonic transducers constituting the ultrasonic pairs have a phase difference of 180°.

That is, a phase difference between the first and second ultrasonic transducers 130a and 130b and third and fourth ultrasonic transducers 140a and 140b is 180°, and a phase difference between the first ultrasonic transducer 130a and the third ultrasonic transducer is 0°.

In addition, an area of the ultrasonic transducer may be greater than or equal to a constant value ($2\pi\lambda d$) such that the length (distance d) of the ultrasonic pair is twice a near field length ($a^2/4\pi\lambda$, for a quadrangle) of the ultrasonic transducer.

That is, in an exclusion mode in which $\lambda=2d$, the area of the ultrasonic transducer may be greater than or equal to $4\pi d^2$ (about $13d^2$), and in the case of a concentration mode in which $\lambda=d$, the area of the ultrasonic transducer may be greater than or equal to $2\pi d^2$ (about $6d^2$).

The configuration of the signal processing unit 300 is the same as the configuration of the signal processing unit of the fluorescence sensor for measuring the microalgae according to the exemplary embodiment of the present invention described with reference to FIG. 1.

The signal processing unit 300 outputs total fluorescence intensity ($I_T$) and turbidity ($i_m$) caused by algae and other particles in a state in which there is no ultrasonic wave in the measurement region, noise fluorescence intensity ($I_N$) and turbidity ($i_p$) caused by other particles which are concentrated in a state in which a node of an ultrasonic wave is formed in the measurement region and thus algae are excluded, and concentrated total fluorescence intensity ($I_{TF}$) and turbidity ($i_a$) in a state in which an antinode of an ultrasonic wave is formed in the measurement region and thus algae are concentrated. In addition, the signal processing unit 300 obtains signal fluorescence intensity ($I_S$) by subtracting the noise fluorescence intensity ($I_N$) from the total fluorescence intensity ($I_{ST}$), obtains concentrated signal fluorescence intensity ($I_{SF}$) by subtracting the noise fluorescence intensity ($I_N$) from the concentrated total fluorescence intensity ($I_{TF}$), and extracts a concentration ratio by dividing the turbidity sum ($i_p+i_a$) in states in which the node and the antinode of the ultrasonic wave are formed in the measurement region by the turbidity ($i_m$) in a state in which there is no ultrasonic wave in the measurement region. Then, by comparing the signal fluorescence intensity ($I_S$) with the noise fluorescence intensity ($I_N$), when the signal fluorescence intensity ($I_S$) is greater than or equal to the noise fluorescence intensity ($I_N$), the signal processing unit 300 calculates a corrected algal density from the signal fluorescence intensity ($I_S$), and when the signal fluorescence intensity ($I_S$) is less than the noise fluorescence intensity ($I_N$), the signal processing unit 300 calculates a corrected algal density from concentrated correction signal fluorescence intensity obtained by dividing the concentrated signal fluorescence intensity ($I_{SF}$) by the concentration ratio.

The fluorescence sensor for measuring the microalgae shown in FIGS. 3 and 4 has the following advantages and disadvantages as compared with the fluorescence sensor for measuring the microalgae shown in FIGS. 1 and 2.

First, since ultrasonic pairs are formed using an ultrasonic transducer and another ultrasonic transducer instead of an ultrasonic transducer and an ultrasonic reflector, a degree of exclusion and concentration of algae is high, which has an advantage in that a measurement limit is low.

In addition, since a degree of concentration of algae is accurately obtained through turbidity measurement, it is possible to increase measurement accuracy even when an algal density of a measurement region is low.

On the other hand, there is a disadvantage in that manufacturing difficulties and costs of a sensor are increased due to the addition of a turbidity measurement unit and an ultrasonic transducer.

Figure 5:
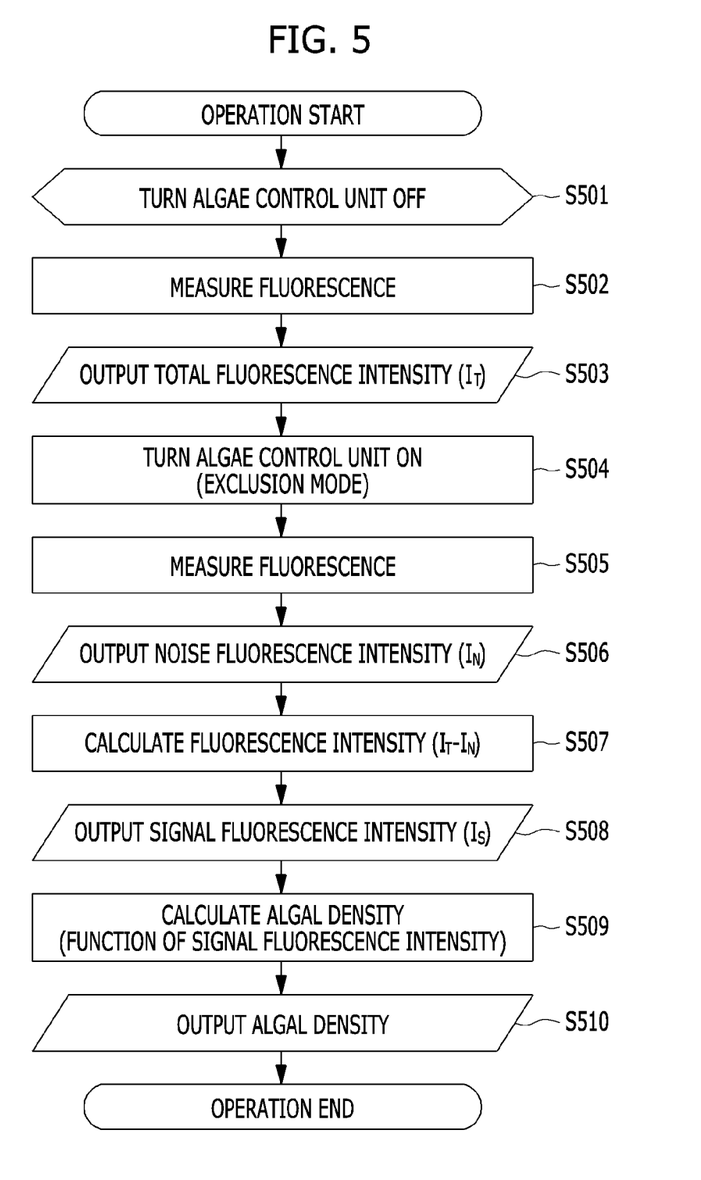
FIG. 5 is a flowchart illustrating a method of operating a fluorescence sensor for measuring microalgae according to an embodiment of the present invention.

FIG. 5 is a flowchart illustrating a method of operating a fluorescence sensor for measuring microalgae according to an embodiment of the present invention.

Referring to FIG. 5, in the method of operating the fluorescence sensor for measuring the microalgae according to the embodiment of the present invention, in a state in which there is no ultrasonic wave in a measurement region (algae control unit OFF, S501), excitation light is irradiated to measure fluorescence (S502) and measure total emitted fluorescence intensity ($I_T$) (S503), a node of an ultrasonic standing wave is formed in the measurement region (S504) to measure fluorescence (S505) and measure noise fluorescence intensity ($I_N$) in a state in which algae are excluded (S506), signal fluorescence intensity ($I_S$) is extracted by subtracting the noise fluorescence intensity from the total fluorescence intensity (S507 and S508), an algal density is calculated from the signal fluorescence intensity (S509), and the algae density is output (S510).

Figure 6A:
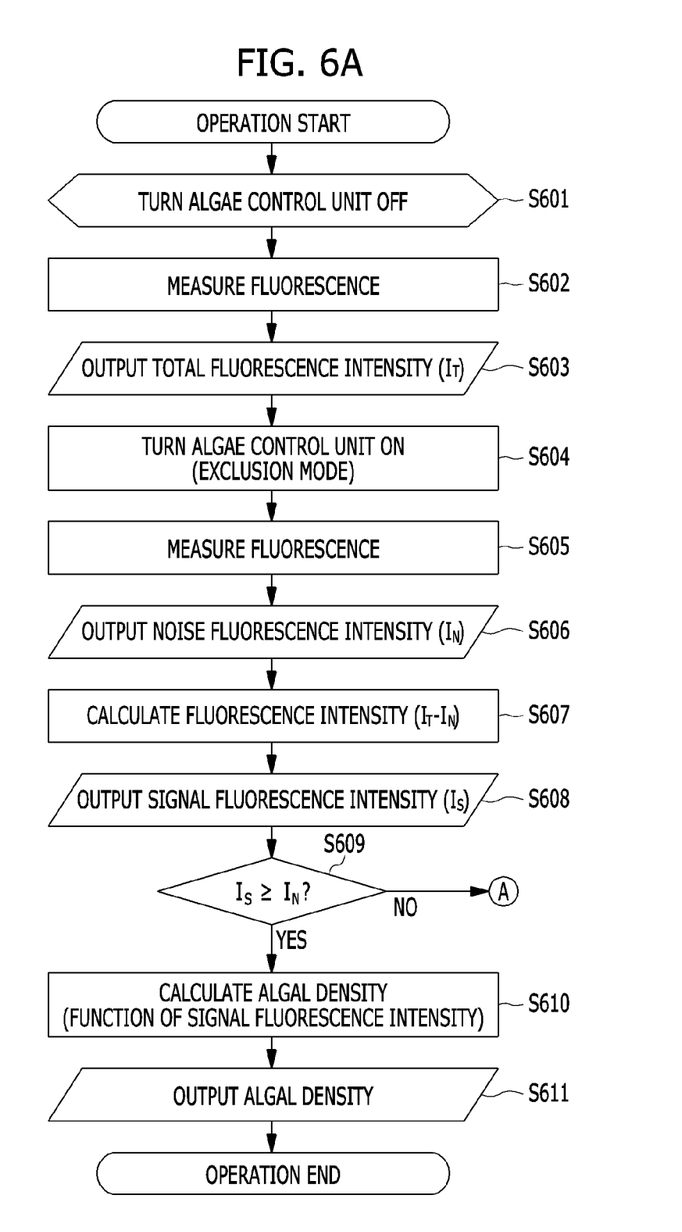
FIG. 6A and FIG. 6B are flowcharts illustrating a method of operating a fluorescence sensor for measuring microalgae according to another embodiment of the present invention.
Figure 6B:
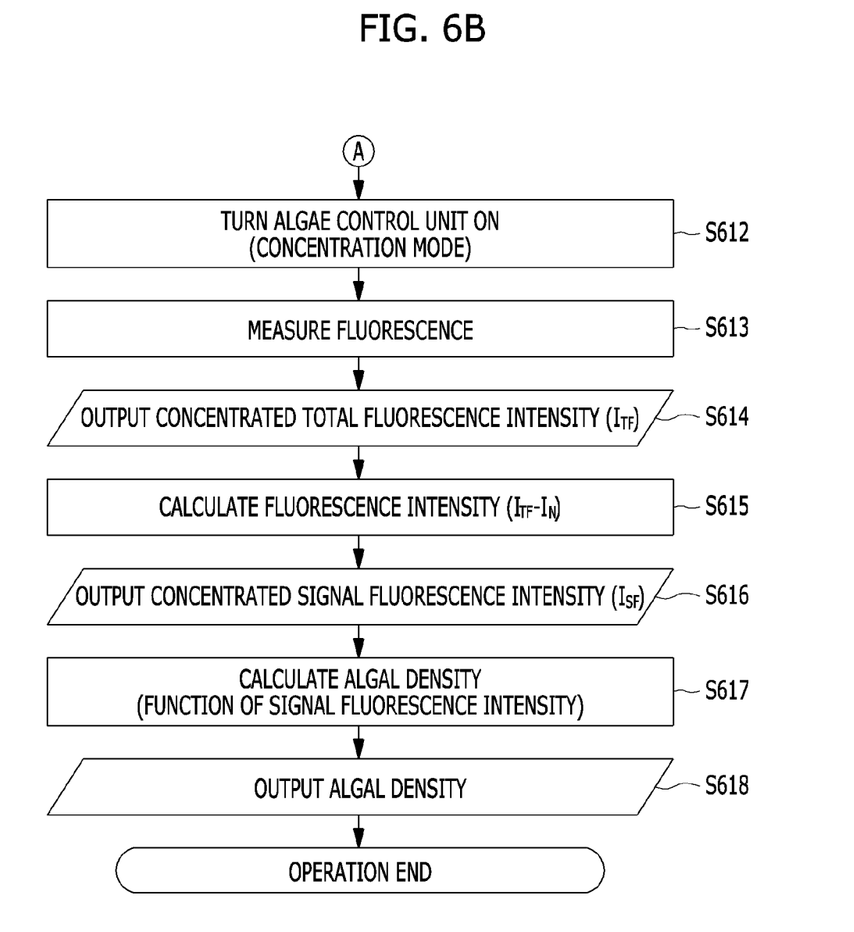

FIG. 6A and FIG. 6B are flowcharts illustrating a method of operating a fluorescence sensor for measuring microalgae according to another embodiment of the present invention.

Referring to FIG. 6A and FIG. 6B, in the method of operating the fluorescence sensor for measuring the microalgae according to another embodiment of the present invention, in a state in which there is no ultrasonic wave in a measurement region (S601), excitation light is irradiated to measure emitted fluorescence (S602) and output total fluorescence intensity ($I_T$) (S603).

Subsequently, in an exclusion mode (algae control unit ON, S604), a node of an ultrasonic standing wave is formed in the measurement region to measure fluorescence (S605) and output noise fluorescence intensity ($I_N$) (S606) in a state in which algae are excluded.

Signal fluorescence intensity ($I_S$) is extracted by subtracting the noise fluorescence intensity from the total fluorescence intensity (S607 and S608), the signal fluorescence intensity ($I_S$) is compared with the noise fluorescence intensity ($I_N$) (S609), and when the signal fluorescence intensity ($I_S$) is greater than or equal to the noise fluorescence intensity ($I_N$), an algal density is calculated from the signal fluorescence intensity ($I_S$) and is output (S610 and S611).

In operation S609, when the signal fluorescence intensity ($I_S$) is less than the noise fluorescence intensity ($I_N$), an antinode of an ultrasonic standing wave is formed in the measurement region to measure fluorescence (S612 and S613) and measure concentrated total fluorescence intensity ($I_{TF}$) in a state in which algae are concentrated (S614).

Subsequently, concentrated signal fluorescence intensity ($I_{SF}$) is extracted by subtracting the noise fluorescence intensity ($I_N$) from the concentrated total fluorescence intensity ($I_{TF}$) (S615 and S616).

Next, an algal density is calculated from the concentrated signal fluorescence intensity ($I_{SF}$) and is output (S617 and S618).

Figure 7A:
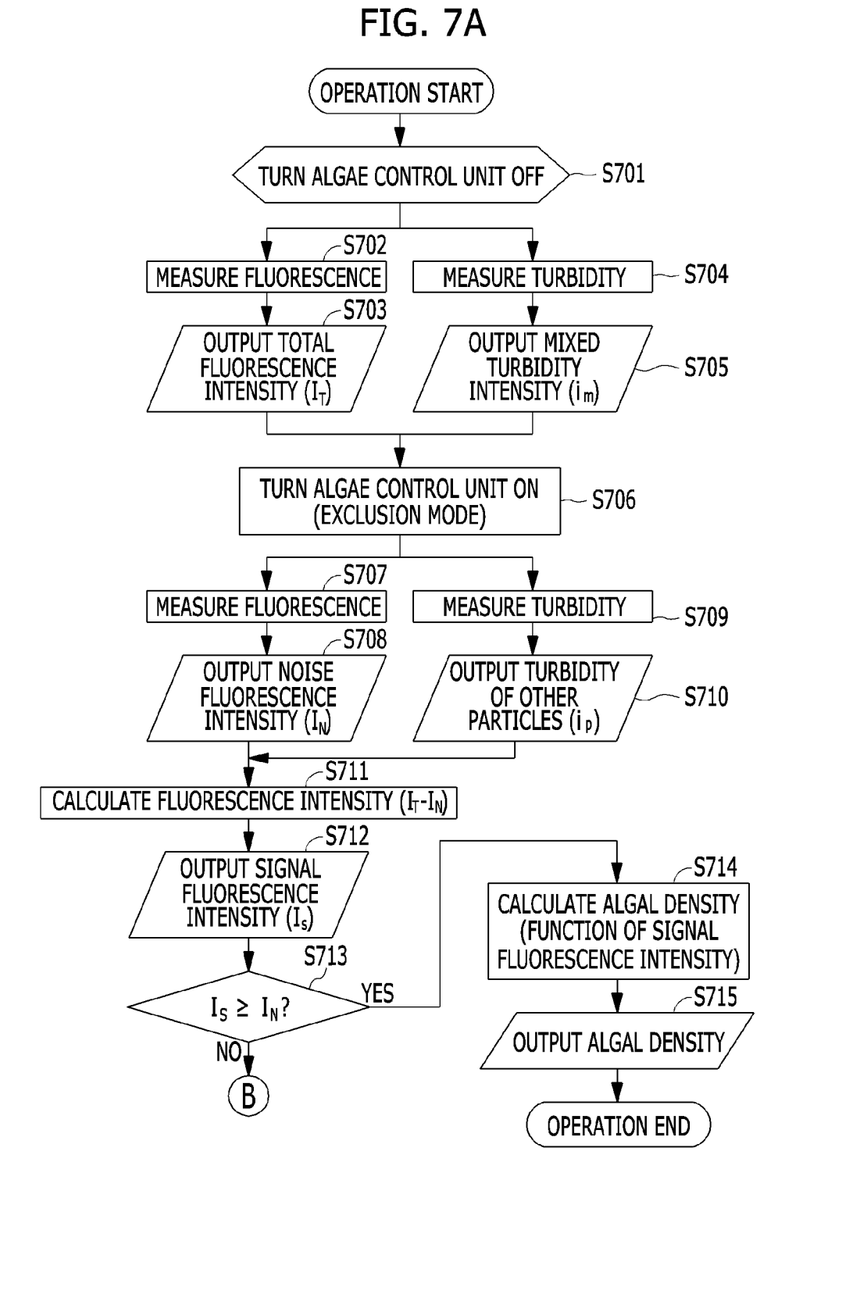
FIG. 7A and FIG. 7B are flowcharts illustrating a method of operating a fluorescence sensor for measuring microalgae according to still another embodiment of the present invention.
Figure 7B:
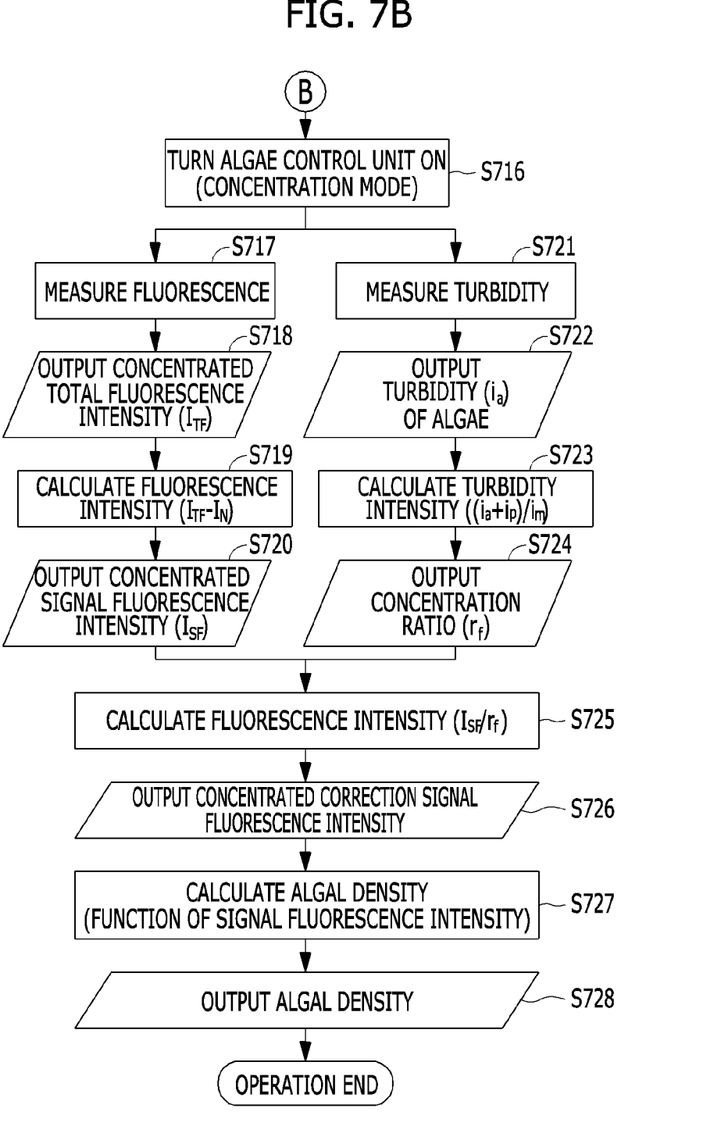

FIG. 7A and FIG. 7B are flowcharts illustrating a method of operating a fluorescence sensor for measuring microalgae according to still another embodiment of the present invention.

Referring to FIG. 7A and FIG. 7B, in a state in which there is no ultrasonic wave in a measurement region (S701), excitation light is irradiated to measure emitted fluorescence and measure total fluorescence intensity ($I_T$) (S702 and S703).

In addition, incident light is irradiated to measure turbidity ($i_m$) caused by algae and other particles (S704 and S705).

A node of an ultrasonic standing wave is formed in the measurement region (S706) to measure fluorescence and measure noise fluorescence intensity ($I_N$) (S707 and S708) in a state in which algae are excluded.

Turbidity ($i_p$) caused by other particles concentrated in a state in which algae are excluded is measured and output (S709 and S710).

In operations S711 and S712, signal fluorescence intensity ($I_S$) is extracted by subtracting the noise fluorescence intensity ($I_N$) from the total fluorescence intensity ($I_T$).

In operation S713, the signal fluorescence intensity ($I_S$) is compared with the noise fluorescence intensity ($I_N$), and when the signal fluorescence intensity ($I_S$) is greater than or equal to the noise fluorescence intensity ($I_N$), an algae density is calculated from the signal fluorescence intensity ($I_S$) and is output (S714 and S715).

As a result of the comparison in operation S713, when the signal fluorescence intensity ($I_S$) is less than the noise fluorescence intensity ($I_N$), in operation S716, an antinode of an ultrasonic standing wave is formed in the measurement region.

In operations S717 and S718, concentrated total fluorescence intensity ($I_{TF}$) is measured in a state in which algae are concentrated, and in operations S721 and S722, turbidity ($i_a$) caused by the algae concentrated in a state in which the algae are concentrated is measured.

In operations S719 and S720, concentrated signal fluorescence intensity ($I_{SF}$) is extracted by subtracting the noise fluorescence intensity ($I_N$) from the concentrated total fluorescence intensity ($I_{TF}$).

In operations S723 and S724, a concentration ratio ($r_f$) is extracted by dividing the turbidity sum ($i_a+i_p$) of algae/other particles in a concentrated state by the turbidity ($i_m$) of the algae/other particles in a normal state.

In operation S725, the concentrated signal fluorescence intensity ($I_{SF}$) is divided by the concentration ratio ($r_f$), in operation S726, concentrated correction signal fluorescence intensity is extracted, and in operations S727 and S728, an algal density is calculated from the concentrated correction signal fluorescence intensity and is output.

On the other hand, a method of operating a fluorescence sensor for measuring microalgae according to embodiments of the present invention may be implemented in a computer system or recorded in a recording medium. The computer system may include at least one processor, a memory, a user input device, a data communication bus, a user output device, and a storage. Each of the above-described components performs data communication through the data communication bus.

The computer system may further include a network interface coupled to a network. The processor may be a central processing unit (CPU) or a semiconductor device for processing a command stored in the memory and/or the storage.

The memory and the storage may include various types of volatile or nonvolatile storage mediums. For example, the memory may include a read-only memory (ROM) and a random-access memory (RAM).

Therefore, the method of operating the fluorescence sensor for measuring the microalgae according to the embodiments of the present invention may be implemented as a computer-executable method. When the method of operating the fluorescence sensor for measuring the microalgae according to the embodiments of the present invention is executed in a computer device, computer-readable commands may perform the method of operating the fluorescence sensor according to the present invention.

Meanwhile, the above-described method of operating the fluorescence sensor for measuring the microalgae according to the present invention may also be embodied as computer-readable codes on a computer-readable recording medium. The computer-readable recording medium includes all types of recording media in which data that can be read by a computer system is stored. Examples of the computer-readable recording media include a ROM, a RAM, a magnetic tape, a magnetic disc, a flash memory, an optical data storage device, and the like. In addition, the computer-readable recording medium may also be distributed over network coupled computer systems so that the computer-readable code may be stored and executed in a distributed fashion.

According to the embodiments of the present invention, an algal density is calculated by extracting only a fluorescence signal caused by a pigment contained in algae excluding fluorescent noise caused by a pigment dissolved in water in a measurement region, thereby acquiring high measurement accuracy.

When an algal density is low in a measurement region, algae are concentrated to increase a fluorescence signal that is less than or equal to fluorescence noise, thereby increasing a measurement lower limit.

The effects of the present invention are not limited to the above, and other effects not described herein will be clearly understood by those skilled in the art from the above detailed description.

So far, the present invention has been described with reference to the embodiments thereof. It should be understood by those skilled in the art that various changes in form and details may be made therein without departing from the spirit and scope of the present invention. Therefore, the disclosed embodiments should be considered in a descriptive sense only and not for purposes of limitation. Also, the scope of the present invention is defined not by the detailed description of embodiments but by the appended claims, and all differences within the scope thereof should be construed as being included in the present invention.

The components described in the example embodiments may be implemented by hardware components including, for example, at least one digital signal processor (DSP), a processor, a controller, an application-specific integrated circuit (ASIC), a programmable logic element, such as an FPGA, other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software. The method according to example embodiments may be embodied as a program that is executable by a computer, and may be implemented as various recording media such as a magnetic storage medium, an optical reading medium, and a digital storage medium. Various techniques described herein may be implemented as digital electronic circuitry, or as computer hardware, firmware, software, or combinations thereof. The techniques may be implemented as a computer program product, i.e., a computer program tangibly embodied in an information carrier, e.g., in a machine-readable storage device (for example, a computer-readable medium) or in a propagated signal for processing by, or to control an operation of a data processing apparatus, e.g., a programmable processor, a computer, or multiple computers. A computer program(s) may be written in any form of a programming language, including compiled or interpreted languages and may be deployed in any form including a stand-alone program or a module, a component, a subroutine, or other units suitable for use in a computing environment. A computer program may be deployed to be executed on one computer or on multiple computers at one site or distributed across multiple sites and interconnected by a communication network. Processors suitable for execution of a computer program include, by way of example, both general and special purpose microprocessors, and any one or more processors of any kind of digital computer. Generally, a processor will receive instructions and data from a read-only memory or a random access memory or both. Elements of a computer may include at least one processor to execute instructions and one or more memory devices to store instructions and data. Generally, a computer will also include or be coupled to receive data from, transfer data to, or perform both on one or more mass storage devices to store data, e.g., magnetic, magneto-optical disks, or optical disks. Examples of information carriers suitable for embodying computer program instructions and data include semiconductor memory devices, for example, magnetic media such as a hard disk, a floppy disk, and a magnetic tape, optical media such as a compact disk read only memory (CD-ROM), a digital video disk (DVD), etc. and magneto-optical media such as a floptical disk, and a read only memory (ROM), a random access memory (RAM), a flash memory, an erasable programmable ROM (EPROM), and an electrically erasable programmable ROM (EEPROM) and any other known computer readable medium. A processor and a memory may be supplemented by, or integrated into, a special purpose logic circuit. The processor may run an operating system (OS) and one or more software applications that run on the OS. The processor device also may access, store, manipulate, process, and create data in response to execution of the software. For purpose of simplicity, the description of a processor device is used as singular; however, one skilled in the art will be appreciated that a processor device may include multiple processing elements and/or multiple types of processing elements. For example, a processor device may include multiple processors or a processor and a controller. In addition, different processing configurations are possible, such as parallel processors. Also, non-transitory computer-readable media may be any available media that may be accessed by a computer, and may include both computer storage media and transmission media. The present specification includes details of a number of specific implements, but it should be understood that the details do not limit any invention or what is claimable in the specification but rather describe features of the specific example embodiment. Features described in the specification in the context of individual example embodiments may be implemented as a combination in a single example embodiment. In contrast, various features described in the specification in the context of a single example embodiment may be implemented in multiple example embodiments individually or in an appropriate sub-combination. Furthermore, the features may operate in a specific combination and may be initially described as claimed in the combination, but one or more features may be excluded from the claimed combination in some cases, and the claimed combination may be changed into a sub-combination or a modification of a sub-combination. Similarly, even though operations are described in a specific order on the drawings, it should not be understood as the operations needing to be performed in the specific order or in sequence to obtain desired results or as all the operations needing to be performed. In a specific case, multitasking and parallel processing may be advantageous. In addition, it should not be understood as requiring a separation of various apparatus components in the above described example embodiments in all example embodiments, and it should be understood that the above-described program components and apparatuses may be incorporated into a single software product or may be packaged in multiple software products. It should be understood that the example embodiments disclosed herein are merely illustrative and are not intended to limit the scope of the invention. It will be apparent to one of ordinary skill in the art that various modifications of the example embodiments may be made without departing from the spirit and scope of the claims and their equivalents.

What is claimed is:

1. A fluorescence sensor for measuring microalgae, comprising:
    a fluorescence measurement unit including a light emitter configured to irradiate excitation light onto a measurement region and a detector configured to measure fluorescence emitted from the measurement region;
    an algae control unit configured to form a node and an antinode of an ultrasonic standing wave in the measurement region to control an algal density; and
    a signal processing unit configured to calculate the algal density using fluorescence intensity signals according to an operation mode of the algae control unit,
    wherein the signal processing unit outputs total fluorescence intensity in a state in which there is no ultrasonic wave in the measurement region, noise fluorescence intensity in a state in which the node is formed in the measurement region, and concentrated total fluorescence intensity in a state in which the antinode is formed in the measurement region and calculates the algal density using signal fluorescence intensity which is a result of subtracting the noise fluorescence intensity from the total fluorescence intensity, and
    wherein:
    when the signal fluorescence intensity is greater than or equal to the noise fluorescence intensity, the signal processing unit calculates the algal density from the signal fluorescence intensity; and
    when the signal fluorescence intensity is less than the noise fluorescence intensity, the signal processing unit calculates the algal density from concentrated signal fluorescence intensity which is a result of subtracting the noise fluorescence intensity from the concentrated total fluorescence intensity.

2. The fluorescence sensor of claim 1, wherein the excitation light includes light having a central wavelength to be absorbed by a component contained in algae, and
the fluorescence includes light having a central wavelength to be emitted by the component contained in the algae.

3. The fluorescence sensor of claim 1, wherein the algae control unit uses an ultrasonic wave in a preset frequency range, and
the algae are moved in a same direction as a traveling direction of the ultrasonic wave.

4. The fluorescence sensor of claim 1, wherein the algae control unit includes a pair of an ultrasonic transducer and an ultrasonic reflector or includes a plurality of pairs of ultrasonic transducers, and
a distance of the pair is included within a preset range.

5. The fluorescence sensor of claim 4, wherein, when the algae control unit includes the plurality of pairs of ultrasonic transducers, the ultrasonic transducers are orthogonally arranged with each other, and alternating currents applied to the ultrasonic transducers have a phase difference of 180°.

6. The fluorescence sensor of claim 4, wherein the algae control unit excludes and concentrates the algae by applying an alternating current having a frequency corresponding to a wavelength which is a preset multiple of the distance and forming the node and the antinode of the ultrasonic standing wave.

7. The fluorescence sensor of claim 4, wherein:
when the algae control unit includes the pair of the ultrasonic transducer and the ultrasonic reflector, an area range of each of the ultrasonic transducer and the ultrasonic reflector is a first preset multiple of a square of the distance; and
when the algae control unit includes the plurality of pairs of ultrasonic transducers, an area range of each of the ultrasonic transducers is a second preset multiple of the square of the distance.

8. The fluorescence sensor of claim 4, wherein, when the algae control unit includes the pair of the ultrasonic transducer and the ultrasonic reflector, the ultrasonic transducer includes a lead zirconate titanate (PZT) ceramic or lead magnesium niobate-lead titanate (PMN-PT) single crystal element, and the ultrasonic reflector includes a titanium metal or copper-titanium alloy plate.

9. A fluorescence sensor for measuring microalgae, comprising:
an optical measurement unit including a fluorescence measurement unit configured to measure fluorescence emitted from a measurement region when excitation light is irradiated onto the measurement region and a turbidity measurement unit configured to measure scattered light emitted from the measurement region when incident light is irradiated onto the measurement region;
an algae control unit configured to form a node and an antinode of an ultrasonic standing wave in the measurement region to control an algal density; and
a signal processing unit configured to calculate the algal density using a fluorescence intensity signal and a scattered light intensity signal according to an operation mode of the algae control unit,
wherein the signal processing unit extracts a concentration ratio by dividing a sum of turbidity in a state in which the node of the ultrasonic standing wave is formed in the measurement region and turbidity in a state in which the antinode is formed, by turbidity in a state in which there is no ultrasonic wave in the measurement region.

10. The fluorescence sensor of claim 9, wherein a center wavelength range of the incident light and the scattered light of the turbidity measurement unit includes a preset length.

11. The fluorescence sensor of claim 9, wherein the signal processing unit outputs total fluorescence intensity in a state in which there is no ultrasonic wave in the measurement region, noise fluorescence intensity in a state in which the node is formed in the measurement region, and concentrated total fluorescence intensity in a state in which the antinode is formed in the measurement region, and
when signal fluorescence intensity, which is a result of subtracting the noise fluorescence intensity from the total fluorescence intensity, is less than the noise fluorescence intensity, the signal processing unit calculates the algal density using concentrated correction signal fluorescence intensity which is a result of dividing concentrated signal fluorescence intensity, which is a result of subtracting the noise fluorescence intensity from the concentrated total fluorescence intensity, by the concentration ratio.

12. A method of operating a fluorescence sensor for measuring microalgae, the method comprising:
(a) measuring total fluorescence intensity emitted by irradiating excitation light in a state in which there is no ultrasonic wave in a measurement region;
(b) measuring noise fluorescence intensity by forming a node of an ultrasonic standing wave in the measurement region;
(c) calculating an algal density using signal fluorescence intensity which is a result of subtracting the noise fluorescence intensity from the total fluorescence intensity,
(d) measuring concentrated total fluorescence intensity by forming an antinode of the ultrasonic standing wave in the measurement region, and
(e) when the signal fluorescence intensity is less than the noise fluorescence intensity, calculating the algal density from concentrated signal fluorescence intensity which is a result of subtracting the noise fluorescence intensity from the concentrated total fluorescence intensity.

13. The method of claim 12, further comprising:
measuring scattered light emitted by irradiating incident light onto the measurement region; and
calculating a concentration ratio by dividing a sum of turbidity in a state in which the node of the ultrasonic standing wave is formed in the measurement region and turbidity in a state in which the antinode is formed, by turbidity in a state in which there is no ultrasonic wave in the measurement region.

14. The method of claim 13, further comprising:
when the signal fluorescence intensity is greater than or equal to the noise fluorescence intensity, calculating the algal density from the signal fluorescence intensity; and
when the signal fluorescence intensity is less than the noise fluorescence intensity, calculating the algal density using concentrated correction signal fluorescence intensity which is a result of dividing concentrated signal fluorescence intensity, which is a result of subtracting the noise fluorescence intensity from the concentrated total fluorescence intensity, by the concentration ratio.

* * * * *